(12) United States Patent
Spottheim et al.

(10) Patent No.: US 7,784,467 B2
(45) Date of Patent: Aug. 31, 2010

(54) SKIN LESION PROTECTOR

(75) Inventors: Ofer Spottheim, 8 Hayovel Street, Raanana (IL) 43401; Daniel Kaufman, Petach-Tikva (IL)

(73) Assignee: Ofer Spottheim, RaAnana (IL)

( * ) Notice: Subject to any disclaimer, the term of this patent is extended or adjusted under 35 U.S.C. 154(b) by 3 days.

(21) Appl. No.: 11/568,716

(22) PCT Filed: May 4, 2005

(86) PCT No.: PCT/IL2005/000468
§ 371 (c)(1),
(2), (4) Date: Nov. 6, 2006

(87) PCT Pub. No.: WO2005/104661
PCT Pub. Date: Nov. 10, 2005

(65) Prior Publication Data
US 2007/0185424 A1    Aug. 9, 2007

Related U.S. Application Data

(60) Provisional application No. 60/567,823, filed on May 5, 2004.

(51) Int. Cl.
*A61F 13/00* (2006.01)
*A61F 13/02* (2006.01)
(52) U.S. Cl. .................. 128/898; 128/888; 602/42; 602/46; 602/48; 424/59; 424/447; 424/448; 250/515.1

(58) Field of Classification Search ............. 602/41–43, 602/46, 48; 424/443, 447–449, 59–60, 78.02, 424/78.03, 429, 445; 606/9; 250/515.1, 250/519.1; 128/858, 888, 890, 898; 2/12, 2/67, 69, 456
See application file for complete search history.

(56) References Cited

U.S. PATENT DOCUMENTS

| 2,851,805 | A | * | 9/1958 | Allen | 132/319 |
| 5,682,607 | A | * | 11/1997 | Klein | 2/9 |
| 5,847,404 | A | * | 12/1998 | Grady | 250/515.1 |
| 6,420,623 | B2 | * | 7/2002 | Augustine et al. | 602/41 |
| 6,548,730 | B1 | * | 4/2003 | Patel et al. | 602/56 |
| 6,817,030 | B2 | * | 11/2004 | Desai | 2/67 |
| 2002/0022008 | A1 | * | 2/2002 | Forest et al. | 424/59 |
| 2002/0086043 | A1 | * | 7/2002 | Gueret | 424/404 |
| 2002/0192270 | A1 | * | 12/2002 | Gueret | 424/443 |

FOREIGN PATENT DOCUMENTS

GB    2444906 A  *  6/2008
WO    WO 02/09630 A1  *  2/2002

* cited by examiner

*Primary Examiner*—Patricia M Bianco
*Assistant Examiner*—Keri J Nicholson

(57) ABSTRACT

An adhesive skin protector that filters sunlight harmful to skin lesions. The protector includes at least one adhesive layer adapted to adhere to an area of skin having a skin lesion; and at least one filter layer attached to said adhesive layer, the at least one filter layer being adapted to filter sunlight harmful to the skin lesion.

5 Claims, 2 Drawing Sheets

SKIN LESION PROTECTOR

RELATED APPLICATIONS

The present application is a US National Phase of PCT Application No. PCT/IL2005/000468 filed on May 4, 2005. The present application also claims the benefit under 119(e) of U.S. Provisional Application No. 60/567,823 filed on May 5, 2004, the disclosure of which is incorporated herein by reference.

FIELD OF THE INVENTION

The invention relates to a protector that adheres to the skin and optionally protects the skin and/or skin lesions from harmful electromagnetic radiation.

BACKGROUND OF THE INVENTION

Electromagnetic radiation from the sun, herein sun or sunlight, for example in the ultraviolet region of the sun's spectrum, is known to cause harm to skin and/or skin lesions. Pigmented lesions, for example moles, may undergo malignant transformation in response to harmful sunlight, resulting in a malignant melanoma, a highly virulent skin cancer than spreads rapidly to vital organs and is often fatal.

Creams that protect the skin against harmful sunlight are known, but may not provide adequate protection for skin lesion for one or more of the following reasons:

i) skin lesions often have a topography comprising fissures, kerinatized skin or elevated areas that resist coverage by protective creams; and ii) skin lesions often project above the surrounding skin divest protective creams as they rub against apparel, for example a robe worn while in transit to a location in the sun.

Skin tapes that have an inadvertent property of blocking sunlight, are known but usually come in a single width and dispense in rectangular patches. When removed following a day in the sun, each patch of tape leaves a large, unsightly, rectangular area of skin that stands out against adjacent tanned areas, making them less desirable for lesion protection.

SUMMARY OF THE INVENTION

An aspect of some exemplary embodiments of the present invention relates to a skin protector comprising a sunlight filter layer that filters one or more wavelengths of sunlight and an adhesive layer adapted to adhere the filter layer to the skin. In an exemplary embodiment, the filter layer is adapted to reduce harmful wavelengths of sunlight, herein harmful sunlight, associated with malignant transformation of moles. Alternatively or additionally, the filter layer is adapted to reduce harmful sunlight to other sunlight-sensitive skin lesions, for example actinic keratoses and/or lesions comprising reduced and/or absent pigmentation, herein vitiligo.

In an exemplary embodiment, the filter layer comprises a spongy material that substantially conforms to uneven skin topography associated with skin lesions and/or surrounding skin. Alternatively or additionally, the filter layer comprises a non-spongy, shape-conforming material that substantially conforms to the topography of the skin lesion and/or skin.

Optionally, the adhesive layer is located around the periphery of the filter layer so the center of the filter layer remains unattached to the skin and/or skin lesion, thereby reducing irritation to the skin and/or lesion. Alternatively or additionally, the peripheral adhesive layer serves to offset the filter layer from the skin so that the filter layer contacts only a portion of the skin lesion. Alternatively or additionally, the filter layer is shaped so that it forms an offset from the skin, thereby only contacting a portion of the skin and/or skin lesion.

In an exemplary embodiment, the center of the filter layer has a greater concentration of filtering material than that of the periphery so that the skin lesion is protected from harmful waves and the surrounding skin receives sunlight that causes tanning.

In an exemplary embodiment, a kit is provided that includes the skin protector in two or more diameters, tanning protection and/or shapes. Alternatively or additionally, the kit includes a mirror that can be used to aid in positioning of the protector in hard-to-visualize areas. Optionally, the kit includes a map of places where a particular user needs to affix a skin protector. The kit optionally includes a sunlight filtering cream that applies prior to sunlight exposure and does not affect the adhesive of the skin protector. Alternatively or additionally, the kit may contain one or more post sun-exposure skin care products, for example skin-moisturizing creams and/or anti-inflammatory lotions.

Optionally, a kit comes in one of several colors, to match various skin tones. Alternatively or additionally, a coloring agent is provided with the kit to color the skin protectors to a desired skin tone.

An aspect of some exemplary embodiments of the present invention relates to a skin protector that adheres to the skin and filters one or more wavelengths of sunlight and contains an artificial tanning preparation that causes the area it protects to increase in pigmentation. Optionally, the tanning preparation is released as a result of body heat, perspiration, time length and/or sunlight so that the skin below the protector tans in a manner that matches the surrounding unprotected skin. Optionally, the preparation or other chemical(s) is provided in a matrix which slowly degrades in heat, in sun and/or in the presences of moisture.

An aspect of some embodiments of the invention relates to using an adhesive band. In an exemplary embodiment of the invention, an adhesive band that is opaque to UV is placed over a plurality and/or substantially all moles or other UV sensitive skin areas. Optionally, a package of adhesive bands, strips and/or patches is provided with an instruction leaflet describing their use on such lesions and/or what lesions to use.

An aspect of some embodiments of the invention relates to decorative local UV protection devices. In an exemplary embodiment of the invention, colored putty is used for placement on lesions or skin areas especially sensitive to UV. In an exemplary embodiment of the invention, an adhesive patch or strip is decorated with images and/or graphics. In an exemplary embodiment of the invention, a tattoo, for example formed of gum and ink, includes UV protection and is optionally adapted with regard to size, shape and/or color to cover a lesion. Optionally, tattoos are provided in a range of sizes or are custom made (e.g., for a particular patient) so that they cover a range of lesion sizes and shapes.

There is thus provided in accordance with an exemplary embodiment of the invention, an adhesive skin protector that filters sunlight harmful to skin lesions, the protector comprising:

at least one adhesive layer adapted to adhere to an area of skin having a skin lesion; and at least one filter layer attached to said adhesive layer, the at least one filter layer being adapted to filter sunlight harmful to the skin lesion, specifically at only part of said protector designated to correspond to said lesion. Optionally, said adhesive layer adheres at said designated part. Optionally, said designated area is 3 mm or less in diameter.

In an exemplary embodiment of the invention, the at least one filter layer is adapted to filter sunlight that causes harmful effects to one or more skin lesions comprising:
- moles;
- actinic keratotic skin lesions;
- biopsy locations; and
- lightly pigmented areas of skin.

In an exemplary embodiment of the invention, the at least one filter layer filters one or more of:
- Ultraviolet-A radiation; and
- Ultraviolet-B radiation.

In an exemplary embodiment of the invention, a healing enhancing material is contained in at least one of the filter layer and the adhesive layer. In an exemplary embodiment of the invention, a tanning enhancement preparation is contained in at least one of the filter layer and the adhesive layer. Optionally, the tanning enhancing preparation is adapted to be gradually released to the skin. Optionally, the tanning enhancing preparation is adapted to release as a result of at least one of:
- time;
- sunlight;
- body heat; and
- perspiration.

In an exemplary embodiment of the invention, the at least one filter layer comprises two or more filter densities;
a first filter density in the center of the filter layer that filters a first amount; and
a second filter density along the periphery of the filter layer that filters a lesser amount such that tanning is possible underlying said second filter density.

In an exemplary embodiment of the invention, the protector comprises one or more materials that substantially conform to skin topography.

In an exemplary embodiment of the invention, the protector comprises one or more spongy materials. Optionally, the one or more spongy materials substantially conform to skin topography.

In an exemplary embodiment of the invention, at least a portion of the protector is adapted to offset from at least a portion of the skin lesion.

In an exemplary embodiment of the invention, the adhesive layer comprises a ring situated around the filter layer periphery. Optionally, the adhesive layer comprises an offset that offsets the filter layer from at least a portion of the skin lesion.

In an exemplary embodiment of the invention, a protector is provided as part of a kit in which the protector is provided in two or more sizes.

In an exemplary embodiment of the invention, a protector is provided as part of a kit in which the protector is provided in two or more shapes.

In an exemplary embodiment of the invention, the protector has an irregular form.

In an exemplary embodiment of the invention, the protector functions as a temporary tattoo.

In an exemplary embodiment of the invention, a kit is provided comprising the protector and including at least one of the following items:
i) a skin moisturizer;
ii) a mirror;
iii) a sunlight filtering cream;
iv) the protector in two or more sizes; and
v) the protector in two or more shapes.

There is also provided in accordance with an exemplary embodiment of the invention an adhesive skin protector that filters sunlight harmful to skin lesions, the protector comprising at least one filter layer adapted to filter sunlight harmful to skin lesions, the filter layer having:
an adhesive adapted to adhere the filter layer to at least a portion of the skin lesion; and
a tanning enhancement preparation. Optionally, the protector filters sunlight harmful to skin.

In an exemplary embodiment of the invention, the tanning enhancing preparation is adapted to be gradually released to the skin. Optionally, the tanning enhancing preparation is adapted to release as a result of at least one of:
- time;
- sunlight;
- body heat; and
- perspiration.

In an exemplary embodiment of the invention, the protector comprises one or more materials that substantially conform to skin topography.

In an exemplary embodiment of the invention, the protector comprises one or more spongy materials. Optionally, the spongy material is adapted to absorb and release a tanning enhancement preparation.

In an exemplary embodiment of the invention, a kit is provided comprising the protector and including at least one of the following items:
i) a skin moisturizer;
ii) a mirror;
iii) a sunlight filtering cream;
iv) the protector in two or more sizes;
v) a tanning enhancement preparation; and
vi) the protector in two or more shapes.

There is also provided in accordance with an exemplary embodiment of the invention, a method for protecting skin comprising a skin lesion from harmful sunlight, the method comprising:
positioning a material that filters harmful sunlight proximate to a skin region comprising a skin lesion;
adhering the filter material to the skin region; and
filtering harmful sunlight. Optionally, adhering comprises using an adhesive.

In an exemplary embodiment of the invention, said filtering filters sunlight at wavelengths that causes harm to one or more of:
- moles;
- actinic keratoses; and
- vitiligo.

In an exemplary embodiment of the invention, the method includes releasing a tanning enhancing preparation from the material. Optionally, said releasing is caused by at least one of:
- time;
- sunlight;
- body heat; and
- perspiration.

In an exemplary embodiment of the invention, said method comprises:
identifying a plurality of UV sensitive lesions; and
applying said filter material to said plurality of lesions in response to an excursion in the sun.

BRIEF DESCRIPTION OF FIGURES

The present invention will be more completely understood and appreciated from the following detailed description of exemplary embodiments of the invention, taken in conjunction with the drawings. Corresponding structures in different drawings are indicated with the same reference numeral. The drawings are.

DETAILED DESCRIPTION OF EXEMPLARY EMBODIMENTS

Figure 1A:
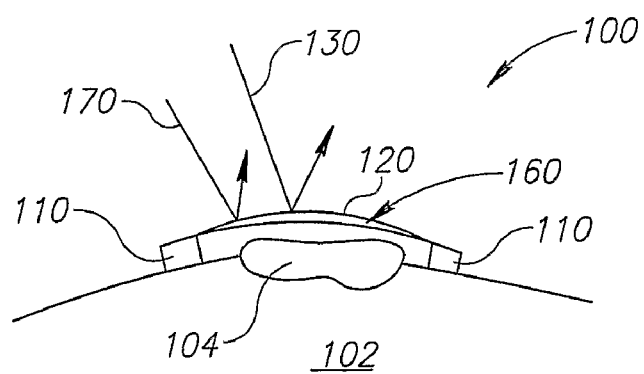
FIGS. 1A-1B and FIG. 2 are schematic views of a skin protector attached to an area of skin, in accordance with an exemplary embodiment of the invention.
Figure 2:
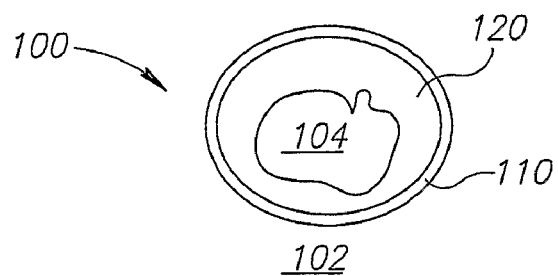

FIGS. 1A and 2 are side and aerial (transparent) schematic views, respectively, of a skin protector 100 attached to an area of skin 102 comprising a skin lesion 104, for example a mole. In an exemplary embodiment, protector 100 comprises an adhesive layer 110 that serves to adhere filter layer 120 to skin 102 and/or skin lesion 104. In an exemplary embodiment, filter layer 120 filters sunlight waves 130 and/or 170 that may cause lesion 104 to undergo malignant transformation when lesion 104 comprises a mole.

Alternatively or additionally filter layer 120 applies to skin 102 and filters waves 130 and/or 170 that are harmful to skin 102 and/or other skin lesions 104, for example waves that cause malignant transformation of actinic keratoses and/or vitiligo (hereinafter referred to generally as "moles"). Sunlight waves 130 and/or 170 that are harmful to skin 102 and/or lesion 104 may comprise Ultraviolet-A radiation and Ultraviolet-B radiation.

In an exemplary embodiment, adhesive layer 110 comprises a ring around the periphery of protector 100 and, for example, offsets at least a portion of the center of filter layer 120 from skin 102 and/or skin lesion 104. By offsetting adhesive layer 110, irritation to skin 102 and/or lesion 104 is reduced. In some embodiments, adhesion to the lesion is allowed, for example for moles. In an alternative embodiment, protector 100 is not layered with both a filter layer and an adhesive layer at adhesive areas 110 and/or at a periphery of protector 100. For example, only adhesive layer 110 may underlay only a backing layer (not shown). For purpose of manufacture, it may be convenient to have the filter layer act as a backing as well. Optionally, the backing layer and/or a filter layer are transparent to one or more visual light waves, for example appearing transparent or translucent.

During exposure to harmful waves 130 and/or 170, it is often desirable that skin 102 around the periphery of skin lesion 104 is exposed to at least limited amounts and or spectrum of sunlight waves 130 and/or 170 so that it pigments and visually blends with skin 102 further away from skin lesion 104. In an exemplary embodiment, the filter density and/or spectral filtration wavelength range in the center of filter layer 120 filters is increased to filter waves 130 and 170 while the filter density and/or filtration in the periphery of filter layer 120 is decreased to allow transmittal at least some waves 170. Optionally, periphery of filter layer 120 filters sunlight that is harmful to skin lesions 104, but not harmful to skin 102.

In an exemplary embodiment, adhesive 110 and/or filter layer 120 contains one or more tanning preparations 160 known to enhance tanning with minimal or no exposure to sun. Preparation 160, for example, contains melanocyte-stimulating compounds that cause skin melanocytes to release melanin, thereby causing skin 102 to become pigmented. With release of preparation 160, the area below protector 100 tans and blends in with surrounding skin 102 that has tanned as a result of exposure to waves 130 and 170.

Alternatively or additionally, a coloring preparation may be provided in skin protector 100. Alternatively or additionally, other preparations, such as antibiotics, disinfectants, healing enhancers or anti-inflammatory materials are provided.

Optionally, tanning preparation 160 is incorporated into protector 100 with a release mechanism so that skin 102 and/or skin lesion 104 increase in pigmentation the longer skin 102 is exposed to sun. In this fashion, skin 102 and/or lesion 104 beneath protector 100 substantially duplicate the pigmentation of surrounding skin 102 that increases in pigmentation with longer exposure to waves 130 and 170. For example, Hydroxyacetone can be used to emulate tanning action.

Optionally, protector 100 is adapted to release preparation 160 gradually during the length of time it is applied to skin 102 and/or lesion 104. Alternatively or additionally, exposure to waves 130 and 170 triggers continued release of preparation 160 so that preparation 160 tans skin 102 and/or lesion 104 only during sun exposure. Alternatively or additionally, body heat and/or perspiration trigger continued release of preparation 160 and/or facilitates absorption of preparation 160 into skin 102 and/or lesion 104.

In an exemplary embodiment of the invention, preparation 160 is contained in a gel matrix or is microencapsulated (or otherwise encapsulated) so that its enclosure degrades under conditions of heat, humidity and/or UV radiation, at a known rate. Alternatively or additionally to tanning related preparations, other chemicals may be provided for example, herbal preparations, homeopathic medicines, chemicals which are known to affect moles, dye and/or paint.

Figure 1B:
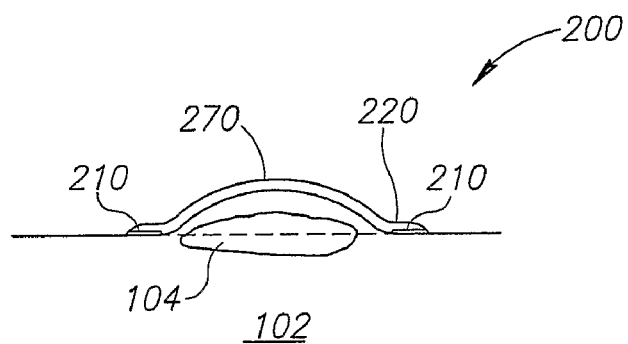

FIG. 1B is a side view of an alternative skin protector 200 in which filter layer 220 is curved (or otherwise protector 200 is non-planar) to create an offset 270 from at least a portion of skin lesion 104 and/or skin 102, thereby reducing irritation to skin 102 and/or lesion 104. Optionally, an adhesive section 210 is flat. Optionally, the curve is provided at manufacture. Optionally, offset 270 is adhesive on its inside so that it can be attached to an underlying skin protrusion.

It should be noted that while FIG. 1A also shows an offset of the skin protector, optionally, the protector is substantially flat with the surface of the skin. In an alternative embodiment, adhesive layer/sections 110 serve to offset the entire protector 100.

Figure 3:
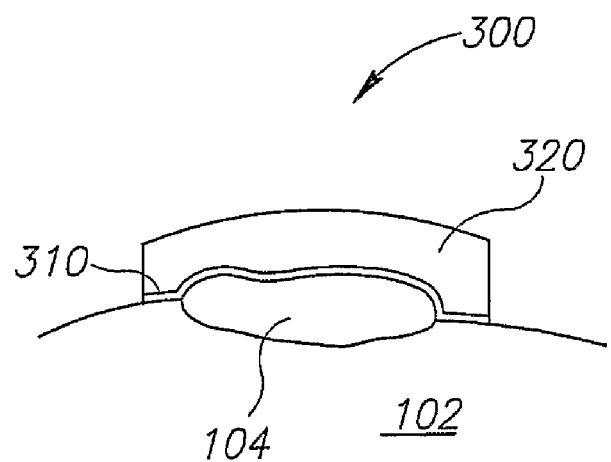
FIGS. 3 and 4 are schematic views of a skin protector attached to an area of skin, in accordance with an alternative exemplary embodiment of the invention.
Figure 4:
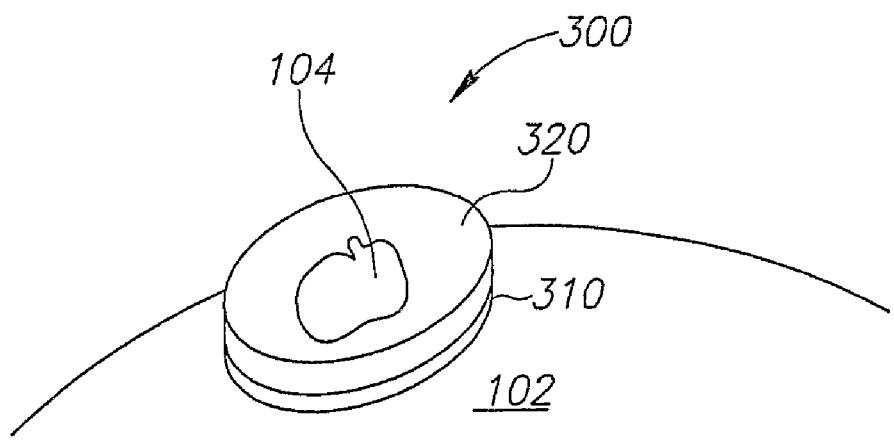

FIGS. 3 and 4 are side and aerial (semi-transparent) schematic views, respectively, of a skin protector 300, comprising a filter layer 320 and adhesive layer 310, in accordance with an alternative exemplary embodiment of the invention.

Optionally, filter layer 320 and/or an adhesive layer 310 comprise one or more materials that substantially conform to the topography of skin 102 and skin lesion 104. For example, adhesive layer 310 and/or filter layer 320 comprise a foam material that forms a substantially negative impression of skin 102 and skin lesion 104 upon application to skin 102. Alternatively or additionally, protector 300 comprises one or more non-spongy resilient materials that substantially conform to the shape of skin 102 and/or skin lesion 104. In one embodiment of the invention, separate adhesive sections and foam sections are provided. In another embodiment, an adhesive layer underlays a foam layer.

In an alternative embodiment of the invention, putty, optionally colored putty, for example formed of a gummy material, is applied to moles. Optionally, a sunblocking material is mixed into the putty. Optionally, color is mixed into the putty or gum.

In an exemplary embodiment, foam-type skin protector 300 contains one or more preparations 160 that are known to enhance tanning with minimal or no exposure to sun, so the area below protector 300 blends in with surrounding tanned skin 102. Optionally, skin protector 300 comprises a material that blocks harmful sunlight from reaching skin 102 and/or lesion 104. Alternatively, protector 300 is opaque to sunlight and blocks all sunlight rays 130 and 170 from reaching skin 102.

In an exemplary embodiment, a kit (not shown) is provided that comprises protector 300 (and/or 100) in two or more diameters adapted to cover two or more sizes of skin lesion 104. For example, at least one of the at least two skin protectors may have a diameter of between 0.5 centimeters and 1.5 centimeters and at least one of the at least two skin protectors may have a diameter of between 1.5 centimeters and 2.5 centimeters. Optionally, the mole covering area is 1 mm, 2 mm, 3 mm, 4 mm, 6 mm, 8 mm or any smaller, intermediate or larger size (diameter). The protector may extend, for example, 1 mm, 2 mm, 3 mm, 4 mm or more past the active area. Optionally, an applicator stick (optionally transparent) is provided, which stick includes a strip of skin protectors, with at least one protector with adhesive exposed. Applying the stick to flesh causes the exposed protector to detach from the stick (optionally being held by a weak adhesive) and attach to the body. Optionally, a next protector is advanced to a contact location on the stick, for example, the protectors being mounted on a strip.

In an exemplary embodiment of the invention, a kit comprises a coloring agent (e.g., ink or food coloring, optionally pre-mixed for certain shades) suitable for coloring the skin protectors, to a matching skin tone. Alternatively or additionally, a plurality of different kits may be available, for example, pre-colored to match various skin tones and/or tanning needs.

Alternatively or additionally the kit comprises protector 300 in two or more shapes adapted to cover two or more shapes of skin lesion 104. For example, skin protector 300 in a round and/or oval shape and protector 300 comprising two adjoining circular areas thereby forming a butterfly-like shape. Other shapes may be provided as well, for example, strip shaped or a shape with ragged edges.

Optionally, protector 300 is provided with one or more of the following properties:

(a) Elasticity, e.g., being made from elastic material.
(b) Breathability, e.g. including vents or being formed of a porous material.
(c) Including a sublimating or otherwise cooling material.
(d) A smooth inner surface.
(e) Be sand-proof, e.g., any slits are narrow and forms a seal.
(f) Use saltwater-proof adhesive.
(g) Include a cupped inner profile, to conform to protruding lesions. Optionally, the inner profile accommodates a projection of 0.5 mm, 1 mm, 2 mm or more. Optionally, the outer profile is flat. Alternatively, it is domed. Optionally, the protector is made of a hollowed foam material.

Alternatively or additionally, the kit includes a mirror that can be used to aid in positioning protector 300 over skin lesion 104 in a hard-to-visualize area of skin 102, for example on a person's back.

Optionally, the kit includes a tube of sunlight filtering cream that, for example, does not affect the protector adhesive 310 and can be applied to skin 102 following application of protector 300, prior to exposure to sunlight.

Optionally, the kit contains one or more post sun-exposure skin care products, for example skin-moisturizing creams and/or anti-inflammatory lotions.

In an exemplary embodiment, the kit contains one or more preparations 160 that are known to enhance or simulate tanning with minimal or no exposure to sun. In an exemplary embodiment, preparations 160 are adapted to impregnate protector 100 and can be added to protector 100 to increase tanning of the area below protector 100.

Optionally, the kit includes a map of a body on which a user can mark locations where a skin protector is required. Optionally, each skin protector includes a lay for protecting the adhesive during storage, which layer may include an adhesive point for attaching to the map. Optionally, a user can order, for example by mail, by facsimile, by e-mail or by drawing a map at an internet WWW site, a kit including one or more personalized sets of skin protectors in sizes and/or colors to match his needs, optionally with a personalized map attached.

In an exemplary embodiment of the invention, a protector, such as protector 100, is made in the form of a temporary tattoo, for example as a mixture of gum (or other adhesive) and dye or ink. Optionally, a sun-blocking material or other materials as described above are mixed into the gum and/or ink or provided as a separate layer. In some embodiments, a UV blocking ink is used in the tattoo. Optionally, a transparent backing layer is provided interconnecting parts of the tattoo. This backing layer may be transparent to one or more UV wavelengths and/or tone or more visual wavelengths.

In an exemplary embodiment of the invention, the tattoo has a complex shape, such as that of a spider web or the outline of a rose. In an exemplary embodiment of the invention, the tattoo is selected so that it merges with the mole, for example including a recess for the mole or including a solid area the size and shape (at least) of the mole (or other lesion). Optionally, a package of such tattoos is provided with various sizes and shapes of protected areas. Optionally, the sun-blocking material is only in the size of the lesion to be protected.

Tattoos have one or more of the optional advantages of attractiveness to the user, (e.g., as compared to possibly "square" looking protectors), durability and decorative effect.

In an alternative embodiment of the invention, sun blocking material is applied to the body under or over the skin protector (or tattoo). Optionally, the adhesive used is capable of adhering over sun-block.

In an exemplary embodiment of the invention, one of the lesions protected is a biopsy lesion. Optionally, the protector includes and elutes pharmaceuticals (or other chemicals) to hasten healing and/or prevent infection of the lesion. For example, the protector can include cortisones, antibiotics, disinfectants and/or growth enhancers. In an exemplary embodiment of the invention, the biopsy lesion is formed by removal of a skin sample for biopsy (e.g., of suspected skin cancer).

It should be noted that it is generally desirable to coat the entire body with sun-blocking materials. However, the skin protector optionally provides extra protection, for example higher SPF, or against missing spots, washing off and forgetting to put on sun block.

Also within the scope of the invention is a kit containing "standard" adhesive bands, strips, tape or patches, packages with usage instructions, suggestions and/or warnings for use as protecting lesions of various kinds against UV radiation.

While the present invention has been described with respect to exemplary embodiments thereof, these embodiments are presented by way of example only and are not meant to limit the scope of the invention which is defined by the claims. Furthermore, embodiments of the invention may incorporate some but not all features of the above exemplary embodiments and may include combinations of features from different embodiments. As used in the claims the terms "comprise" or "include" and their conjugations shall mean "including but not necessarily limited to."

It will be appreciated by a person skilled in the art that the present invention is not limited by what has thus far been described. Rather, the scope of the present invention is limited only by the following claims:

The invention claimed is:

1. A method for protecting skin comprising a skin lesion from harmful sunlight, the method comprising:
    identifying a UV sensitive skin lesion from a group consisting of a mole, an actinic keratose, a biopsy location, and a vitiligo; and
    adhering a selected protector to block harmful sunlight proximate to said UV sensitive skin lesion;
    wherein said adhering blocks harmful sunlight for protecting said UV sensitive skin lesion therefrom.

2. A method according to claim 1 wherein adhering comprises using an adhesive.

3. A method according to claim 1 including releasing a tanning enhancing preparation from the material.

4. A method according to claim 3 wherein said releasing is caused by at least one of:
    time;
    sunlight;
    body heat; and
    perspiration.

5. A method according to claim 1, wherein said identifying comprises:
    identifying a plurality of UV sensitive lesions; and
    applying said filter material to said plurality of lesions in response to an excursion in the sun.

* * * * *